US008207109B2

(12) United States Patent
Gaetani

(10) Patent No.: US 8,207,109 B2
(45) Date of Patent: Jun. 26, 2012

(54) FOOD SUPPLEMENT WITH A SLIMMING EFFECT

(75) Inventor: Franco Gaetani, Rome (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 352 days.

(21) Appl. No.: 10/250,361

(22) PCT Filed: Jun. 13, 2001

(86) PCT No.: PCT/IT01/00304
§ 371 (c)(1),
(2), (4) Date: Jul. 1, 2003

(87) PCT Pub. No.: WO02/060278
PCT Pub. Date: Aug. 8, 2002

(65) Prior Publication Data
US 2004/0028668 A1  Feb. 12, 2004

(30) Foreign Application Priority Data
Jan. 29, 2001 (IT) .............................. RM2001A0044

(51) Int. Cl.
*A01N 43/04* (2006.01)
(52) U.S. Cl. ........... 514/1.1; 514/52; 514/276; 514/355; 514/460; 424/400; 424/439; 424/451; 424/464; 424/489; 424/450; 424/752

(58) Field of Classification Search ............... 514/2, 52, 514/226, 355, 460; 424/400, 439, 451, 464; 424/489, 752, 450
See application file for complete search history.

(56) References Cited

U.S. PATENT DOCUMENTS

| 4,298,601 | A   |   | 11/1981 | Howard |
|-----------|-----|---|---------|--------|
| 4,602,039 | A   |   | 7/1986  | Cavazza |
| 5,626,849 | A   | * | 5/1997  | Hastings et al. ............. 424/752 |
| 5,912,272 | A   |   | 6/1999  | Sauermann et al. |
| 5,952,379 | A   |   | 9/1999  | Fassi |
| 5,976,568 | A   | * | 11/1999 | Riley ............................. 424/451 |
| 5,997,915 | A   | * | 12/1999 | Bailey et al. .................... 426/72 |
| 5,998,457 | A   | * | 12/1999 | Kaddurah-Daouk ......... 514/392 |
| 6,217,898 | B1  | * | 4/2001  | Cavazza ........................ 424/450 |
| 6,277,842 | B1  | * | 8/2001  | Carthron ....................... 514/188 |
| 6,562,869 | B1  | * | 5/2003  | Hamilton et al. ............. 514/557 |
| 6,780,851 | B1  | * | 8/2004  | Cavazza .......................... 514/55 |
| 6,861,447 | B2  | * | 3/2005  | Moldenhauer et al. ....... 514/460 |

FOREIGN PATENT DOCUMENTS

| WO | 94 01006 A | 1/1994 |
| WO | 97 46512 A | 11/1997 |
| WO | 01 21208 A | 3/2001 |

OTHER PUBLICATIONS

Database WPI, Section Ch, Week 199121, Derwent Publications., London, GB; AN 1991-156382, XP002179290, & ZA 9 004 021 A (Vander Linde L), Feb. 27, 1991 abstract.
Trademark Registration No. 2226936 "Enerdyn".
Vargiu, R. et al., "Enhacement of muscular performance by a coformulation of propionyl-L-carnitine, coenzyme Q10, nicotinamide, riboflavin and pantothenic acid in the rat" Physiology & Behavior, 76 (2002), 257-263.

* cited by examiner

*Primary Examiner* — Blaine Lankford, Jr.
(74) *Attorney, Agent, or Firm* — Lucas & Mercanti, LLP

(57) ABSTRACT

A food supplement with a "slimming" effect is disclosed which strengthens the skeletal muscle, protecting the cardio-vascular apparatus of the user, and has as its characterising components propionyl L-carnitine, coenzyme $Q_{10}$ nicotinamide, riboflavin and pantothenic acid.

12 Claims, No Drawings

FOOD SUPPLEMENT WITH A SLIMMING EFFECT

The present invention relates to the use as a "slimming" agent (a term which will be better defined here below) of an energy-giving food supplement disclosed and claimed in Italian patent application RM 2000 A 000165 filed in the name of the same applicant on Apr. 4, 2000 (hereinafter referred to as the "previous application") and therefore not available to the public at large at the time of filing of the present application. All the disclosures of the previous application are incorporated herein by reference.

The food supplement disclosed in the previous application meets a need perceived particularly by those users who engage, even as amateurs, in intense physical activity aimed at enhancing their muscular structure.

A substantial percentage of these users comprise individuals who are no longer young, or may be decidedly elderly, who rarely undergo medical examinations aimed at ascertaining their fitness for the physical activity they engage in and at establishing the limits in terms of intensity and effort beyond which it would be dangerous for them to push themselves. The cardiovascular system is particularly at risk in such individuals.

The food supplement described in the previous application is suitable both for exerting an energy-giving, enhancing effect on the skeletal muscles and for simultaneously exerting a protective and tonicising effect on the user's cardiovascular system.

This food supplement comprises the following components as its essential active ingredients, either in combination or packaged separately:
(a) propionyl L-carnitine or a pharmacologically acceptable salt thereof;
(b) coenzyme $Q_{10}$;
(c) nicotinamide;
(d) riboflavin, and
(e) pantothenic acid.

The supplement may additionally contain:
(f) a "carnitine" selected from the group comprising L-carnitine, acetyl L-carnitine, butyryl L-carnitine, valeryl L-carnitine and isovaleryl L-carnitine, or their pharmacologically acceptable salts; and/or
(g) an amino acid selected from the group comprising valine, leucine and isoleucine or mixtures thereof; and/or
(h) a creatine selected from the group comprising creatine and phosphocreatine or mixtures of the same.

What is meant by pharmacologically acceptable salts are, in addition to the so-called "inner salts", salts with acids that do not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerol phosphate; glucose phosphate; lactate; maleate, acid maleate; mucate (galactarate); orotate; oxalate, acid oxalate; sulphate, acid sulphate; trichloroacetate; trifluoroacetate and methane sulphonate.

A list of such pharmacologically acceptable acids approved by the FDA is given in *Int. J. of Pharm.* 33, 1986, 201-217, the latter publication being incorporated herein by reference.

For the preparation of solid administration forms such as, for example, tablets, pills, capsules and granulates, the use of non-hygroscopic salts is preferred. The preferred non-hygrosopic salts of propionyl L-carnitine and, when present, of the other alkanoyl L-carnitines are the mucates (or galactarates) described in U.S. Pat. No. 5,952,379, which is incorporated herein by reference.

Whenever L-carnitine is present in the above-mentioned solid administration forms, the preferred L-carnitine salt is the acid fumarate described in U.S. Pat. No. 4,602,039 which is incorporated herein by reference.

In the food supplement, which may present itself in the form of tablets, pills, capsules or granulates, the weight-to-weight ratios of (a):(b):(c):(d):(e) range from 10:0.04:0.08:0.08:0.4 to 1:4:10:4:20, and preferably from 10:2:5:2:2 to 1:1:4:1:5.

In the unit dosage form, the food supplement may contain:

| | | | | |
|---|---|---|---|---|
| propionyl L-carnitine | from | 50 mg | to | 2,000 mg |
| coenzyme $Q_{10}$ | from | 5 mg | to | 200 mg |
| nicotinamide | from | 10 mg | to | 500 mg |
| riboflavin | from | 5 mg | to | 200 mg |
| pantothenic acid | from | 10 mg | to | 1,000 mg. |

A particularly preferred form (which hereinafter will be referred to by the trade name Enerdyn®) consists of tablets, each of which containing:

| | |
|---|---|
| propionyl L-carnitine | 250 mg |
| coenzyme $Q_{10}$ | 20 mg |
| nicotinamide | 50 mg |
| riboflavin | 20 mg |
| pantothenic acid | 20 mg. |

It has now been found that the above-mentioned food supplement is endowed with a potent "slimming" effect. It should be clearly understood that what is meant by "slimming" effect is not that the supplement brings about an anorexia-inducing effect in the subjects taking it, but that these subjects manifest a weight loss while at the same time conserving unchanged eating habits or that they maintain constant weight despite being on a diet enriched with carbohydrates or fats which, without taking the supplement, would cause an increase in their body weight, even of substantial proportions.

This effect is surprising, since, owing to the skeletal muscle enhancement induced by taking the food supplement, one would expect an increase in body weight as a result of the greater density of muscular as compared to adipose tissue.

The "slimming" activity exerted by the food supplement appears evident from the results of a number of tests on laboratory animals described here below. These tests were chosen in such a way as to be predictive of the efficacy of the food supplement in man.

The composition of the food supplement called Enerdyn® was used for the tests.

Effect of Enerdyn® on Body Weight and on the Ingestion of Food in the Rat

Twenty-four rats subdivided into 4 groups of 6 rats each and treated (orally) with a suspension of Enerdyn® (10 mg/ml) in a solution of carboxymethylcellulose (0.5%) were used.

Each group of animals received a daily dose of Enerdyn® for 7 days according to the following regimen:

The first group of animals was treated with a solution of carboxymethylcellulose with a volume proportional to their body weight (10 ml/kg). This group constituted the control group.

The second group was treated with an Enerdyn® dose of 12.5 mg/kg.

The third group was treated with an Enerdyn dose of 25 mg/kg.

The fourth group was treated with an Enerdyn® dose of 50 mg/kg.

Measurement of Body Weight and the Amount of Food Ingested

During the treatment period, body weight and the amount of food ingested were recorded daily for each rat using a WEDO 2000, 2000 g/1 g scale.

RESULTS

On comparing the growth curves of the control animals and the animals treated with increasing doses of Enerdyn®, a progressive reduction in body weight was observed in the latter with the increase in dose.

On considering the percentage variations in body weight reduction in the three groups of rats treated with Enerdyn® at doses of 12.5, 25 and 50 mg/kg as compared to controls, it was found that the percentage values increased with the increase in dose. In fact, the mean decrease obtained in terms of the relationship between the weekly reductions and the number of weeks of treatment proved dose-dependent with values of 4.75%, 6.12% and 8.125%, respectively, at the doses of 12.5, 25 and 50 mg/kg.

Considering the mean weekly values of the amount of food ingested by the control rats and the rats treated with Enerdyn®, the results obtained show no appreciable differences between the control group rats and those treated with different doses of Enerdyn®. It was noted, however, that in the rats treated with the 25 and 50 mg/kg doses, the amount of food ingested at treatment weeks 6 and 7 was greater than that recorded in the control rats.

DISCUSSION OF THE RESULTS AND CONCLUSIONS

The results obtained indicate that the body growth curves of the treated animals, though being qualitatively similar to those of the control animals, present lower mean values. The decrease in body weight observed in the treated animals is dose-dependent, ranging from a minimum (4.75%) at the 12.5 mg/kg dose to a maximum (8.125%) at the 50 mg/kg dose.

This "slimming" is not attributable to the amount of food ingested by the animals, since no appreciable difference was observed between the mean amounts of food ingested by the treated and control rats.

It is also very interesting to note that, at weeks 6 and 7, the groups of rats treated with the 25 and 50 mg/kg doses not only presented a decrease in body weight, but also ingested a larger amount of food than the control rats.

Though, for the purposes of the invention described herein, it is not necessary to provide theoretical interpretations of a physiological nature, the data obtained in the tests described above suggest that Enerdyn® induces an enhancement of the oxidative metabolic pathways in experimental animals with a consequent increase in cellular energy reserves (increased ATP production). The increased energy available is promptly used by the cells for their activities. In this connection, it has also been observed that, in in-vivo and in-vitro experiments, the muscle cells increase their contractile activity. The enhanced oxidative metabolism induces the use of a greater amount of energy substrates which may stem from an exogenous source (food) or from an endogenous source (lipid reserves).

If the animal uses the former, the greater energy production corresponds to a greater ingestion of food. If the animal is fed normally, the oxidative metabolism draws on endogenous substrates (lipids) with a consequent decrease in body weight.

In conclusion:

1) The body weight of the treated animals does not increase in any of the experimental conditions adopted.

2) If the animals are fed normally, a weight reduction is observed.

3) If the animals are overfed, this energy supplement does not build up as an energy reserve. The increased energy availability due to enhancement of the oxidative pathways induced by Enerdyn® is promptly used by the functional mechanisms of the cells.

The invention claimed is:

1. A method of inducing an overall weight loss in a subject or maintaining a constant weight with a diet enriched in carbohydrates or fats, without contemporarily having an anorexia-inducing effect and without changing the eating habits, in addition, leading to skeletal muscle enhancement in the subject, the method comprising administering to a subject a dietary composition consisting of:
   a. propionyl L-carnitine or a pharmacologically acceptable salt thereof;
   b. coenzyme Q10;
   c. nicotinamide;
   d. riboflavin; and
   e. pantothenic acid,
wherein the weight ratio (a):(b):(c):(d):(e) ranges from 10:0.04:0.08:0.08:0.4 to 1:4:10:4:20; thereby inducing an overall weight loss or maintaining a constant weight in said subject because of increased oxidative metabolism of muscle cells.

2. The method of claim 1, wherein the weight ratio (a):(b):(c):(d):(e) ranges from 10:2:5:2:2 to 1:1:4:1:5.

3. A method of inducing an overall weight loss in a subject or maintaining a constant weight with a diet enriched in carbohydrates or fats, without contemporarily having an anorexia-inducing effect and without changing the eating habits, in addition, leading to skeletal muscle enhancement in the subject, the method comprising administering to a subject a dietary composition consisting of:
   a. propionyl L-carnitine or a pharmacologically acceptable salt thereof;
   b. coenzyme Q10;
   c. nicotinamide;
   d. riboflavin;
   e. pantothenic acid, and at least one member of elements f), g) and h) below
   f. a carnitine selected from the group consisting of L-carnitine, acetyl L-carnitine, valeryl L-carnitine, isovaleryl L-carnitine and butyryl L-carnitine or a pharmacologically acceptable salt thereof;
   g. an amino acid selected from the group consisting of valine, leucine and isoleucine or mixtures thereof;
   h. a creatine selected from the group consisting of creatine and phosphocreatine or mixtures thereof;
wherein the weight ratio (a):(b):(c):(d):(e) ranges from 10:0.04:0.08:0.08:0.4 to 1:4:10:4:20; thereby inducing an overall weight loss or maintaining a constant weight in said subject because of increased oxidative metabolism of muscle cells.

4. The method of claim 3, wherein the weight ratio (a):(b):(c):(d):(e) ranges from 10:2:5:2:2 to 1:1:4:1:5.

5. The method of claim 1, wherein the dietary composition is in unit dosage form and consists of:

| | | |
|---|---|---|
| a. Propionyl L-carnitine | from | 50 mg to 2,000 mg |
| b. coenzyme Q10 | from | 5 mg to 200 mg |
| c. nicotinamide | from | 10 mg to 500 mg |
| d. riboflavin | from | 5 mg to 200 mg |
| e. pantothenic acid | from | 10 mg to 1,000 mg. |

6. The method of claim 5, wherein the dietary composition has the following composition:

| | |
|---|---|
| a. Propionyl L-carnitine | 250 mg |
| b. coenzyme Q10 | 20 mg |
| c. nicotinamide | 50 mg |
| d. riboflavin | 20 mg |
| e. pantothenic acid | 20 mg. |

7. A method of inducing an overall weight loss in a subject or maintaining a constant weight with a diet enriched in carbohydrates or fats without contemporarily having an anorexia-inducing effect and without changing the eating habits, in addition, leading to skeletal muscle enhancement in the subject, the method comprising administering to a subject a dietary composition consisting of:

| | | |
|---|---|---|
| a. Propionyl L-carnitine | from | 50 mg to 2,000 mg |
| b. coenzyme Q10 | from | 5 mg to 200 mg |
| c. nicotinamide | from | 10 mg to 500 mg |
| d. riboflavin | from | 5 mg to 200 mg |
| e. pantothenic acid | from | 10 mg to 1,000 mg; | thereby inducing an overall weight loss or maintaining a constant weight in said subject because of increased oxidative metabolism of muscle cells.

8. A method of inducing an overall weight loss in a subject or maintaining a constant weight with a diet enriched in carbohydrates or fats, without contemporarily having an anorexia-inducing effect and without changing the eating habits, in addition, leading to skeletal muscle enhancement, in the subject, the method comprising administering to a subject a dietary composition in unit dosage form consisting of:

| | |
|---|---|
| a. Propionyl L-carnitine | 250 mg |
| b. coenzyme Q10 | 20 mg |
| c. nicotinamide | 50 mg |
| d. riboflavin | 20 mg |
| e. pantothenic acid | 20 mg; | thereby inducing an overall weight loss or maintaining a constant weight in said subject because of increased oxidative metabolism of muscle cells.

9. A method of inducing an overall weight loss in a subject or maintaining a constant weight with a diet enriched in carbohydrates or fats, without contemporarily having an anorexia-inducing effect and without changing the eating habits, in addition, leading to skeletal muscle enhancement in the subject, the method comprising administering to a subject a dietary composition consisting of:
   a. propionyl L-carnitine or a pharmacologically acceptable salt thereof;
   b. coenzyme Q10;
   c. nicotinamide;
   d. riboflavin; and
   e. pantothenic acid,
wherein the weight ratio (a):(b):(c):(d):(e) ranges from 10:0.04:0.08:0.08:0.4 to 1:4:10:4:20 and wherein the ingredients are administered admixed together or separately; thereby inducing an overall weight loss or maintaining a constant weight in said subject because of increased oxidative metabolism of muscle cells.

10. The method of claim 9, wherein the weight ratio (a):(b):(c):(d):(e) ranges from 10:2:5:2:2 to 1:1:4:1:5.

11. A method of inducing an overall weight loss in a subject or maintaining a constant weight with a diet enriched in carbohydrates or fats, without contemporarily having an anorexia-inducing effect and without changing the eating habits, in addition, leading to skeletal muscle enhancement in the subject, the method comprising administering to a subject a dietary composition consisting of:
   a. propionyl L-carnitine or a pharmacologically acceptable salt thereof;
   b. coenzyme Q10;
   c. nicotinamide;
   d. riboflavin;
   e. pantothenic acid, and
   f. a carnitine selected from the group consisting of L-carnitine, acetyl-L-carnitine, valeryl-L-carnitine, isovaleryl-L-carnitine and butyryl-L-carnitine or a pharmacologically acceptable salt thereof or mixtures thereof; and/or;
   g. an amino acid selected from the group consisting of valine, leucine and isoleucine or mixtures thereof;
   h. a creatine selected from the group consisting of creatine and phosphocreatine or mixtures thereof,
wherein the weight ratio (a):(b):(c):(d):(e) ranges from 10:0.04:0.08:0.08:0.4 to 1:4:10:4:20 and wherein the ingredients are administered admixed together or separately; thereby inducing an overall weight loss or maintaining a constant weight in said subject because of increased oxidative metabolism of muscle cells.

12. The method of claim 11, wherein the weight ratio (a):(b):(c):(d):(e) ranges from 10:2:5:2:2 to 1:1:4:1:5.

* * * * *